United States Patent [19]

Conner et al.

[11] Patent Number: 4,648,867
[45] Date of Patent: Mar. 10, 1987

[54] TAMPON SYSTEM AND METHOD

[75] Inventors: James M. Conner, Old Greenwich, Conn.; Daniel K. Harden, Brooklyn, N.Y.; Donald M. Genaro, Haworth, N.J.

[73] Assignee: Henry Dreyfuss Associates, New York, N.Y.

[21] Appl. No.: 842,377

[22] Filed: Mar. 19, 1986

Related U.S. Application Data

[63] Continuation of Ser. No. 751,425, Jul. 3, 1985, abandoned.

[51] Int. Cl.⁴ ............................................. A61F 13/20
[52] U.S. Cl. ....................................... 604/14; 604/904
[58] Field of Search ................................... 604/11–18, 604/904, 289; 206/363, 438, 440

[56] References Cited

U.S. PATENT DOCUMENTS

| | | | |
|---|---|---|---|
| 3,358,686 | 12/1967 | Asaka | 604/14 |
| 3,486,504 | 12/1969 | Austin, Jr. | 604/289 |
| 3,857,394 | 12/1974 | Alemany | 604/304 |
| 4,360,020 | 11/1982 | Hitchcock, Jr. et al. | 604/289 |
| 4,421,504 | 12/1983 | Kline | 604/14 |

FOREIGN PATENT DOCUMENTS

| | | | |
|---|---|---|---|
| 0104039 | 3/1984 | European Pat. Off. | 604/12 |
| 2233980 | 1/1975 | France | 604/11 |

Primary Examiner—John D. Yasko
Attorney, Agent, or Firm—Fitzpatrick, Cella, Harper & Scinto

[57] ABSTRACT

An improved tampon system includes a tampon, a sheath which surrounds the tampon and is open at one end, a broad-collared ring with an opening therein for passage of the tampon and the sheath, and a closure which is removably secured over the opening in the ring.

16 Claims, 8 Drawing Figures

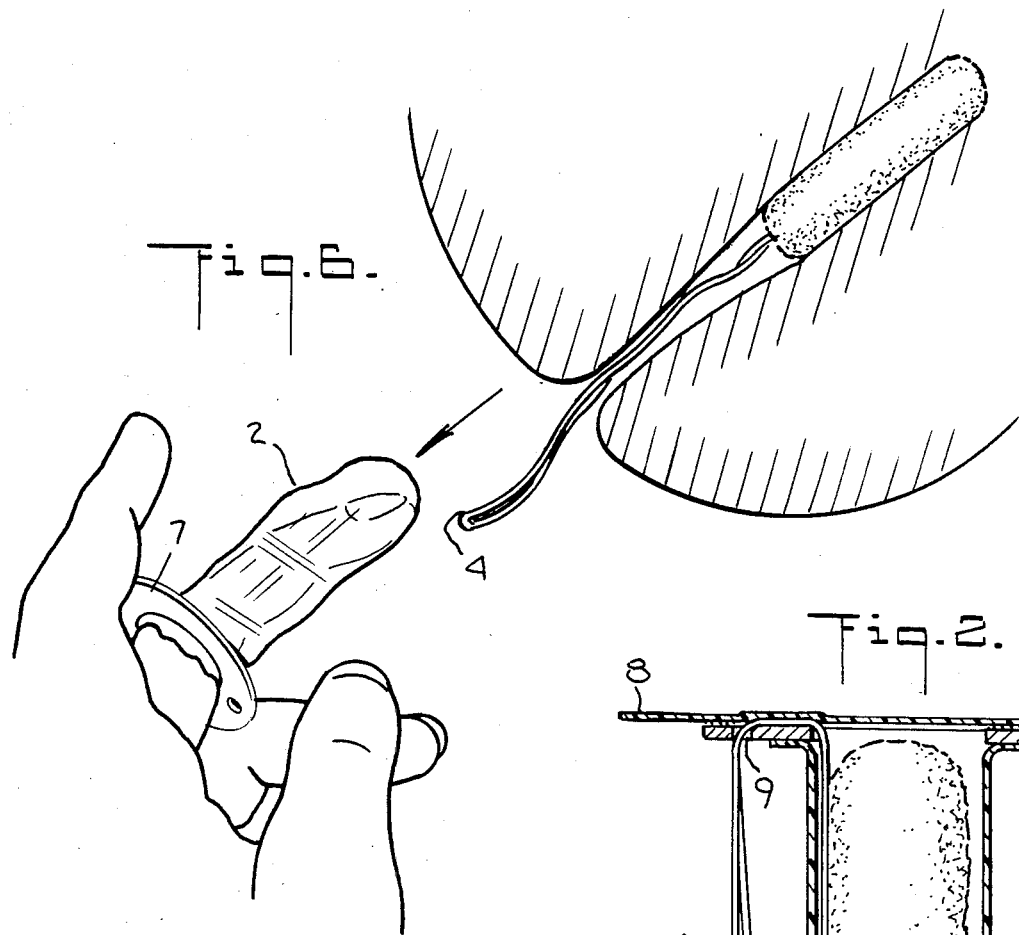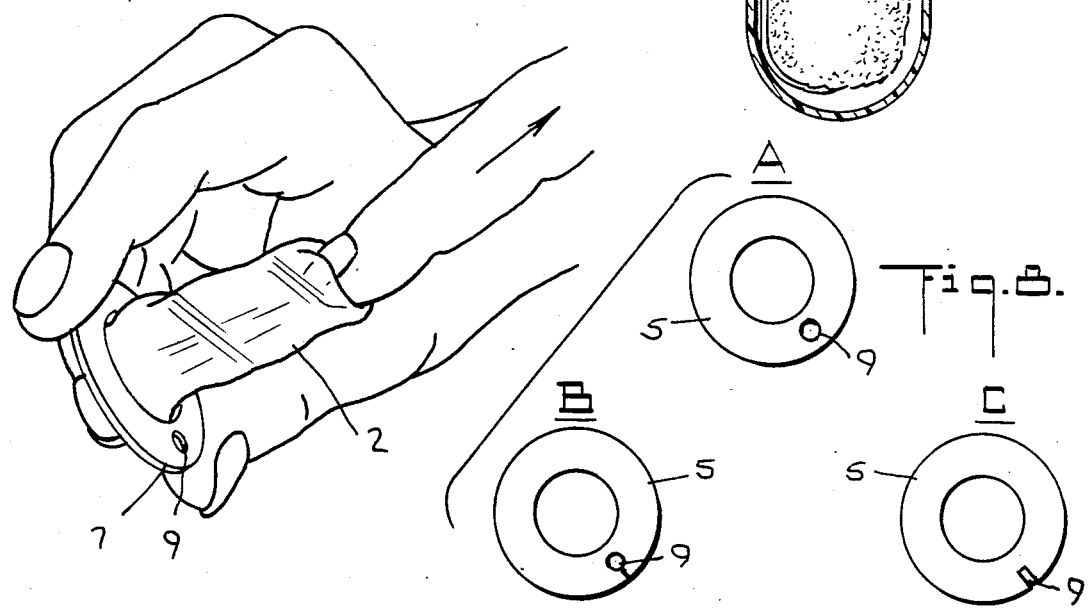

TAMPON SYSTEM AND METHOD

This application is a continuation of application Ser. No. 751,425 filed July 3, 1985, now abandoned.

BACKGROUND OF THE INVENTION

1. Field of the Invention

This invention relates to tampons, particularly to catamenial receptors and more particularly to an improved tampon system which comprises (i) a package for sanitary storage of a tampon, (ii) a sheath for sanitary digital insertion, and (iii) means for sanitary disposal of the insertion device.

2. Description of the Prior Art

For many years catamenial tampons have been used as a replacement for sanitary napkins. The most widely accepted method of insertion is by use of insertion devices, but these tampons may also be inserted by direct placement using one's hand. Insertion devices generally include an outer insertion tube, a tampon positioned therein, and a pusher tube, which is placed behind the tampon and within the outer tube. These insertion devices are themselves placed into the vagina or other bodily opening and withdrawn along with or subsequent to the insertion of the tampon.

Insertion by direct placement has the disadvantage of soiling caused by contact between one's hand and the body or bodily opening. While insertion devices may reduce the likelihood or degree of such contact, they constitute a foreign object which some find offensive or uncomfortable inside the body even temporarily. Moreover, prior art insertion devices may not permit the same ease of insertion, location, or comfort as direct insertion because of difficulties in controlling placement of the tampon. In addition, the insertion device becomes soiled which may make its disposal difficult.

A tampon container has been proposed in U.S. Pat. No. 3,358,686, which, if constructed, would comprise a pliable bag to hold the tampon and a semi-rigid plate with four slots therein placed over the open end of the bag. As referred to there, the tampon would be pushed through the pointed flaps in the plate created by the four slots. That container, however, would not provide sanitary protection for the tampon because debris could enter through the slotted openings. Moreover, the sheath and finger could not pass through the slotted openings. The design and location of the pointed flaps created by the slotted openings would be such that, if the bag or a finger were pushed through the slotted openings, the bag or the finger could not be retracted. Upon attempted retraction, the pointed flaps would grip the sheath and finger and tend to prevent their withdrawal.

SUMMARY OF THE INVENTION

As will be appreciated, the system of this invention provides a sanitary package and permits digital insertion for ease of insertion and precise, comfortable placement with little or no contact between hand and body or body openings and hence with little or no soiling. It also permits sanitary disposal of the used insertion device.

The present invention comprises three elements in a single assembly: a sanitary package, a tampon, and a sanitary insertion device. The system includes a tampon, a sheath which has an extended cylindrical shape and is closed at one end, a broad-collared ring which has a clear opening therein, and a thin, flat closure which is removably secured over the opening in the ring. The cylindrical sheath surrounds the tampon and has its open end secured to the ring adjacent the opening in the ring such that the sheath may be turned inside-out by passage through the ring and then turned right-side-out to its original position by passage back through that opening. The opening in the ring is sufficiently large and clear that it permits passage of the tampon as well as passage and withdrawal of the sheath and a finger.

The present invention invention also includes a method for inserting a tampon that comprises the steps of placing a tampon inside a sheath which is capable of surrounding it and is open at one end; securing the open end of the sheath to a broad-collared ring which has an unobstructed passage for a finger and sheath and also for withdrawal of the finger and sheath, such that the sheath may return to its original position; removably securing a closure over the opening in the ring; removing the removable closure; placing the ring adjacent a bodily opening, such as the vagina; inserting the tampon by digital pressure and passage of a finger and the sheath through the opening in the broad-collared ring; removing the finger from the ring and returning the sheath to its original position.

The system of this invention provides several advantages over the prior art. By its combination of sheath and closure, the tampon system of this invention provides a completely sanitary package. For example, tampon devices of this invention may be carried loose in a handbag without danger of contaminating the tampon or the surfaces of the insertion device. The system also permits sanitary, one-handed direct insertion of the tampon. The broad collared ring provides a shield at the time of insertion, reducing or eliminating contact between hand and body. The opening and sheath permit complete digital insertion while protecting the finger from soiling. After insertion, as the finger is drawn back through the opening in the ring, the sheath may be drawn back through the ring as well, placing the soiled portion inside and making neat disposal possible, particularly if the closure is of a resealable kind and can be returned to its original place after the tampon has been inserted.

As an additional and feature of this invention, a second opening may be provided in the ring through which a tampon withdrawal string may be loosely led. This second opening, which is spaced apart from the first opening, may be in the form of a hole, a slit, a slit ending in a hole, or a notch, as desired. By placing the withdrawal string through this opening, during insertion of the tampon the free end of the string is prevented by friction between the ring and the body from entering the body opening. Upon removal of the ring from adjacent the body, the string is drawn from this opening, leaving it in proper position for later use. In addition, the second opening may be so located that the closure covers and secures it, and the sanitary nature of the package before use is not compromised.

BRIEF DESCRIPTION OF THE DRAWINGS

FIG. 2 is a cross-section of FIG. 1 taken at 2—2 in FIG. 1.

FIGS. 4 to 7 are in partial perspective and partial cross-section and show use of the tampon system of FIG. 1.

FIGS. 8A, 8B and 8C show variations of the broad-collared ring of this invention.

DESCRIPTION OF THE PREFERRED EMBODIMENT

Figure 3:
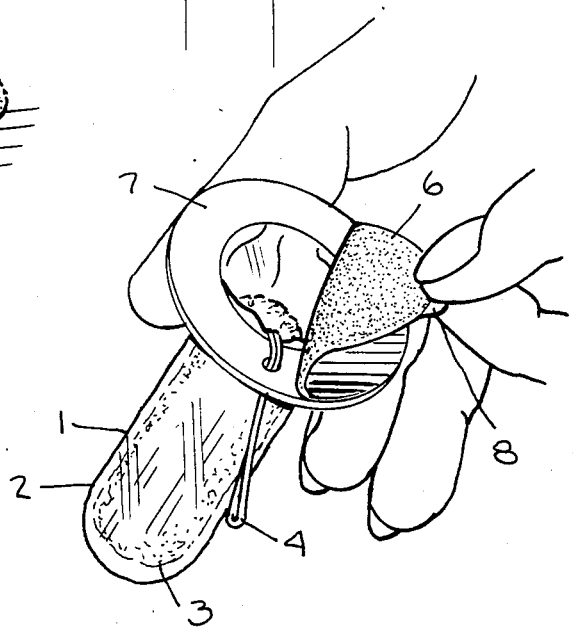
FIG. 3 is a perspective of a tampon system of FIG. 1 with the closure partially removed.

Referring now specifically to the drawings, reference numeral 1 identifies a tampon system of the present invention, which includes a protective sheath 2 (semi-transparent in these drawings but which may preferably be opaque), a tampon 3, and a withdrawal string 4. Reference numeral 5 refers to the combination of the broad-collared ring 7 and the removable closure 6 with its tab 8. As shown in FIGS. 2 and 3, the withdrawal string 4 passes through second opening 9.

Figure 1:
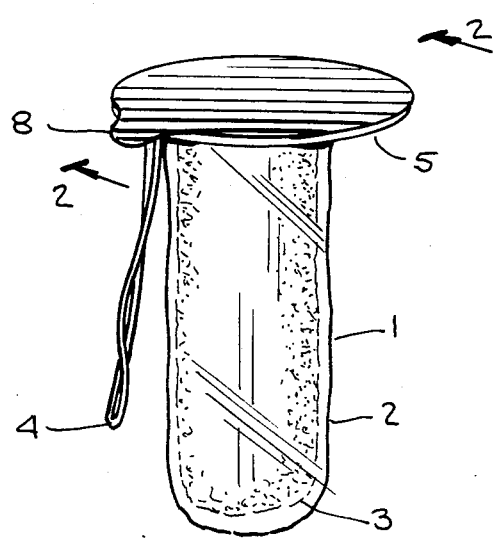
FIG. 1 is a perspective of a tampon system constructed in accordance with the present invention.
Figure 4:
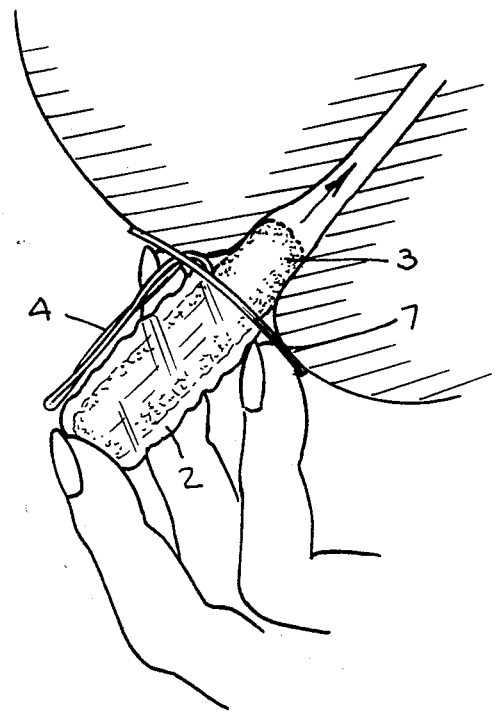
Figure 5:
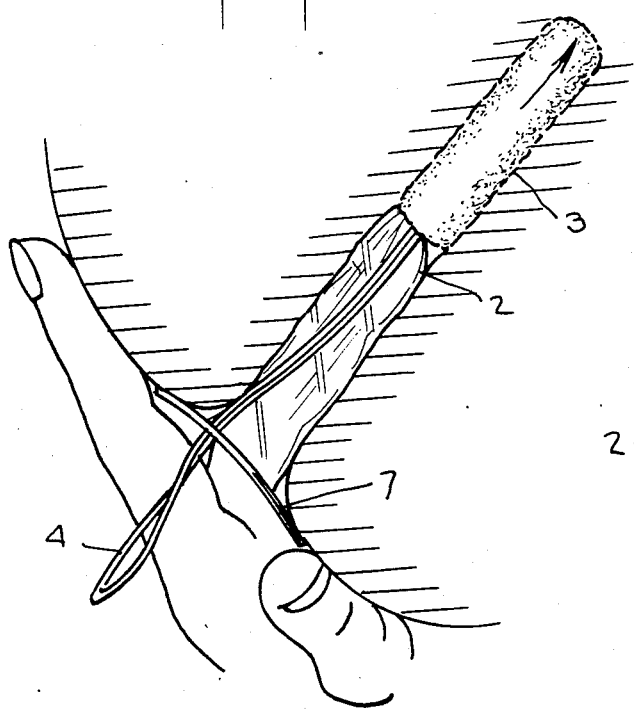

FIG. 3 shows the removal of the closure 6 by pulling on its tab 8 to peel it off of broad collared ring 7. As shown in FIGS. 4 and 5, during insertion the ring can reduce or eliminate contact between the outside of the body and the hand. In FIG. 5, the tampon is fully inserted, and the sheath and finger have passed fully through the clear opening in the broad-collared ring 7. Tactile feed back eases adjustment and optimum placement. The withdrawal string 4 is now outside the sheath and in its proper location held by the ring 7 in its opening 9. The broad-collared ring, by providing a stop, facilitates one-handed insertion.

As is apparent, the surface of the sheath which was originally on the exterior has made no contact with the body orifice. Only the previously interior and sanitary surface has made such contact. In addition, the inserting finger has made no contact with the body orifice.

In FIG. 6, the tampon is shown in place, with the sheath and ring removed from the body. FIG. 7 shows the finger being removed from the tampon insertion device, which is being returned to its original orientation with respect to the ring, thus placing the soiled surface inside.

The tampon may be a standard tampon made of cotton or other absorbent material in the conventional shape for tampons. The sheath may be made of latex, treated paper or other synthetic or natural flexible, thin material. The broad-collared ring may be made of cardboard or other flat, thin, rigid or semi-rigid material, with the sheath adhered by adhesive onto the collar or held between two laminated pieces which may be used to make up the broad-collared ring. The closure may be made of paper, foil, or other similar material, and is removably secured to the ring by use of a peelable adhesive or other securing means. Alternatively, the closure and the ring may be cut from the same piece of material in a dumb-bell shape, with the closure folded over to cover the opening in the ring. If the closure is made of a properly selected material, such as a foil, the package can be made tamper-proof. All parts of the tampon system are preferably biodegradable.

Exemplary dimensions of the system for the ring are an overall diameter of one and one-half inches, with an opening seven-eighths of an inch in diameter, a tampon length of about two inches, which is the length of a standard tampon, and a sheath of about 2½ inches in length and seven-eighths of an inch in diameter.

The foregoing is considered illustrative of the principles of the invention. Variations and modifications will be recognized, and it is hence not desired or intended to limit the invention to the exact construction and procedures described. Rather, all appropriate modifications and equivalents may be used.

We claim:

1. A tampon system comprising;
   a tampon;
   an impermeable sheath which surrounds the tampon and is open at one end, said sheath being unattached to said tampon;
   a broad-collared ring (i) which has an unobstructed opening therein for passage and withdrawal of a finger and the sheath and (ii) to which the open end of the sheath is affixed such that the opening in the sheath registers with the opening in the ring; and
   a sanitary sealing closure which is removably secured over the opening in the ring, the above elements being arranged such that
   (a) the portion of the sheath which contacts the bodily opening is kept sanitary,
   (b) the tampon, the sheath, and a finger can pass through the opening for digital insertion and location of the tampon,
   (c) while inserting the tampon, the finger is protected by the impermeable sheath from soiling, and
   (d) the sheath can be retracted through the opening to provide for clean disposal of the used sheath.

2. The tampon system of claim 1 in which the tampon includes a withdrawal string and the ring includes a second opening spaced apart from the first opening in the ring, said string being led from the tampon out of the sheath through the first opening and then back in the opposite direction through the second opening.

3. The tampon system of claim 1 in which the closure is peelable.

4. The tampon system of claim 3 in which the closure is resealable.

5. A device for sanitary packaging and insertion of a tampon, comprising,
   a sheath which is open at one end, said sheath being unattached to said tampon;
   a broad-collared ring with an unobstructed opening therein to which the sheath is affixed in a location such that the sheath and tampon can pass through the opening therein and the sheath can then be retracted back through said opening; and
   a sealing closure which is secured over the opening in the ring.

6. A device for sanitary packaging and insertion of a tampon, comprising,
   a sheath which is open at one end;
   a broad-collared ring with an unobstructed opening therein to which the sheath is secured in a location such that the sheath can pass through the opening therein and then be retracted back through said opening; and a closure which is secured over the opening in the ring,
   in which device the ring includes a second opening spaced apart from the first opening.

7. The tampon system of claim 1 in which the tampon is a catemenial tampon.

8. A method of inserting a tampon comprising the steps of:
   placing a tampon inside an impermeable sheath which is capable of surrounding the tampon, is not attached to said tampon, and is open at one end;
   affixing at the open end of the sheath a broad-collared ring which has an unobstructed opening therein that permits unobstructed passage and withdrawal of a finger and the sheath and return of the sheath to its original position;

removably securing a sealing closure over the opening in the ring;

removing the removable closure;

placing the broad-collared ring adjacent a bodily opening;

inserting the tampon by means of digital pressure on the sheath and passage of a finger free from soiling and the sheath through the opening in the broad-collared ring;

contacting the bodily opening only with sanitary portions of the sheath;

withdrawing the sheath from the bodily opening; and removing the finger from the broad-collared ring.

9. The method of claim 8 including the additional step of returning the sheath to its original position.

10. The tampon system of claim 1 in which the sheath, the ring and the closure in combination constitute a sanitary package for the tampon and provide sanitary protection to the portion of the sheath which contacts the interior of the bodily opening.

11. The tampon system of claim 1 in which the sheath, the ring and the closure in combination constitute a sanitary, impermeable package for the tampon.

12. The tampon system of claim 1 in which the closure is planar, impermeable, and arranged such that before removal it provides sanitary protection to the tampon.

13. The tampon system of claim 1 in which the broad-collared ring is flat.

14. The tampon system of claim 12 in which the opening in the ring remains unobstructed without application of radial pressure on the ring.

15. The device of claim 5 in which the broad-collared ring is flat, thin, and sufficiently rigid to maintain an unobstructed opening without application of force.

16. The process of claim 8 which includes the step of selecting a closure which is planar and impermeable, and arranging said closure such that before removal it provides sanitary protection to the tampon.

* * * * *